(12) United States Patent
Heindl et al.

(10) Patent No.: US 6,875,850 B2
(45) Date of Patent: Apr. 5, 2005

(54) REAGENT FOR LABELLING NUCLEIC ACIDS

(75) Inventors: Dieter Heindl, Tutzing (DE); Gregor Sagner, Penzberg (DE); Heribert Maerz, Paehl (DE); Herbert Von Der Eltz, Weilheim (DE)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 507 days.

(21) Appl. No.: 09/943,411

(22) Filed: Aug. 30, 2001

(65) Prior Publication Data

US 2002/0110691 A1 Aug. 15, 2002

(30) Foreign Application Priority Data

Sep. 8, 2000 (DE) .......................................... 100 44 373

(51) Int. Cl.[7] .............................. C07H 19/00; C12Q 1/68
(52) U.S. Cl. .......................................... 536/22.1; 435/6
(58) Field of Search .............................. 536/22.1; 435/6

(56) References Cited

U.S. PATENT DOCUMENTS

| | | | |
|---|---|---|---|
| 5,141,837 A | 8/1992 | Nguyen et al. | 430/135 |
| 5,451,463 A | 9/1995 | Nelson et al. | 428/402 |
| 5,624,711 A | 4/1997 | Sundberg et al. | 427/261 |

FOREIGN PATENT DOCUMENTS

| | | | |
|---|---|---|---|
| EP | 0786468 A2 A3 | 7/1997 | ........... C07H/21/00 |
| WO | WO92/11388 | 7/1992 | ........... C12Q/1/68 |
| WO | WO 92/11388 | 7/1992 | ........... C12Q/1/68 |
| WO | WO97/46707 | 12/1997 | ........... C12Q/1/68 |

OTHER PUBLICATIONS

Asseline et al. "Solid Phase Preparation of 5',3'–heterobifunctional Oligodeoxynucleotides Using Modifed Solid Supports" Tetrahedron (1992) 48(7): 1233–54.*

Dubey, Igor et al., "Modification of the Thiourea Linkage of a Fluorescein–Oligonucleotide Conjugate to a Guanidinium Motif during Ammonia Deprotection", Bioconjugate Chem. 1998, vol. 9, pp 627–632 (6) pp.

Igor Dubey, et al., "Modification of the Thiourea Linkage of a Fluorescein–Oligonucleotide Conjugate to a Guanidinium Motif during Ammonia Deprotection", Bioconjugate Chem. 1998, 9, 627–632.

P.K. Ghosh, et al., "Advances in tionalization of Polymer Supports for Synthesis and Modification of oligonucleotides" J. Indian Chem. Soc., vol. 75, Apr. 1998, pp. 206–218.

Ahmad Hansan et al., "Photolabile Protecting Groups for Nucleosides: Synthesis and Photodeprotection Rates" Tetrahedron, vol. 53, No. 12, pp. 4247–4264, 1997.

H. Schaller, et al.. "Studies on Polynucleotides. XXIV. The Stepwise Synthesis of Specific Deoxyribopolynucleotides (4). Protected Derivatives of Deoxyribonucleosides and New Syntheses of Deoxyribonucleoside–3 Phosphates", Syntheses of Deoxyribonucleside–3 Phosphates, Dec. 5, 1963, pp. 3821–3827.

M.S. Shchepinov, et al., "Steric Factors Influencing Hybridisation of Nucleic Acides to Oligonucleotide Arrays" 1997 Oxford University Press, Nucleic Acids Research, 1997, vol. 25, No. 6 (pp. 1155–1161).

Christian Wojczewski, et al., "Fluorescent Oligonucleotides– Versatile Tools as Probes and Primers for DNA and RNA Analysis" Synlett 1999, No. 10, 1667–1678.

* cited by examiner

*Primary Examiner*—Jean C. Witz
*Assistant Examiner*—Susan Hanley
(74) *Attorney, Agent, or Firm*—Marilyn Amick; Roche Diagnostics Operations, Inc.

(57) ABSTRACT

The present invention concerns a labelling reagent in which the label is bound via an amide bond and a linker to a residue of the molecule which is essentially characterized in that the N atom of the amide bond and the label are linked together directly by a covalent bond. In particular these are phosphoramidites or reactive supports suitable for nucleic acid synthesis. The invention also concerns processes for the production of such supports from suitable precursors.

7 Claims, 2 Drawing Sheets

REAGENT FOR LABELLING NUCLEIC ACIDS

The invention is derived from the field of labelling nucleic acids that have been prepared synthetically.

PRIOR ART

Synthetic (deoxy)-oligonucleotides which have been provided with a detectable label are necessary to carry out a broad spectrum of diverse molecular biological and molecular diagnostic methods.

Synthetic (deoxy)-oligonucleotides are usually prepared on a solid phase with the aid of phosphoramidite chemistry. Glass beads having pores of a defined size (abbreviated in the following as CPG=controlled pore glass) are usually used as the solid phase. The first monomer is bound to the support via a cleavable group such that the free oligonucleotide can be cleaved after the solid phase synthesis is completed. The first monomer additionally contains a protected hydroxyl group, dimethoxytrityl (DMT) being usually used as the protective group. The protective group can be removed by acid treatment. Then 3'-phosphoramidite derivatives of (deoxy)-ribonucleosides that are also provided with a DMT protective group are then coupled in a cyclic process to each successive reactive group after is has been freed of the DMT protective group.

According to the prior art so-called trifunctional support materials are used to prepare oligonucleotides that are labelled at the 3' end. For this a trifunctional spacer with two reactive hydroxyl groups and an additional reactive group, preferably an amino group, is firstly prepared. After introducing a DMT protective group on a hydroxyl group, the detectable label is coupled to the reactive amino group of the trifunctional spacer in a second step of the synthesis. However, alternatively the detectable label is not only coupled to the trifunctional spacer via a reactive amino group but also via a third hydroxyl group or an SH group (U.S. Pat. No. 5,451,463; WO 92/11388).

In a third step the trifunctional spacer is bound via its hydroxyl group that is still free to the linking group of the solid phase material that is provided with a separable bond.

Alternatively the detectable label is not coupled until after the actual oligonucleotide synthesis (U.S. Pat. No. 5,141, 837). However, since this requires multiple independent coupling reactions, such a production process is laborious, costly and cannot be automated.

Labelled phosphoramidites in which the marker group is linked to the phosphoramidite via a $C_{3-12}$ linker are usually used to synthesize oligonucleotides labelled at the 5' end.

Hence detectable labels can also be introduced by the phosphoramidite strategy (Synlett 1999, 10, 1667–1678). The same trifunctional spacers can be used for this as for the synthesis of CPG materials. Instead of binding one of the hydroxyl groups to the solid phase, this hydroxyl group is converted into a phosphoramidite in this process. The resulting phosphoramidite can be used for oligonucleotide synthesis like a standard amidite. In principle such phosphoramidites can also be used for internal labelling by replacing a standard nucleoside phosphoramidite by a fluorophore-labelled phosphoramidite during the synthesis cycle. However, it is preferably used for 5' labelling since internal labelling interrupts the base pairing in the strand.

Oligonucleotides provided with a fluorescent label such as fluorescein are often used in molecular biology, such as for the real-time measurement of PCR reactions (WO 97/46707). The fluorescent dyes can be coupled to the amino group of the trifunctional spacer in two different ways according to the prior art:

On the one hand the fluorescent dye, which can itself optionally be provided with cleavable protective groups for protection during the oligonucleotide synthesis, is reacted in the form of an isothiocyanate with the amino group to form a thiourea bond. However, this has the disadvantage that such a thiourea bond is not stable during oligonucleotide synthesis and thus it is not possible to achieve high synthesis yields of fluorescently labelled oligonucleotides (Bioconjugate Chemistry 1998, 9, 627–632). In an alternative process the N-hydroxysuccinimide ester (NHS-ester) of a fluorophore-carboxylic acid is reacted with the free amino group of the spacer to form an amide bond. However, it has turned out that due to the electron-acceptor effect of the amide bond, the spectral properties of the fluorescent dye are changed such that the emission spectrum of an amide-coupled derivative is shifted to higher wavelengths compared to the emission spectrum of a thiourea-coupled derivative.

Hence the object of the present invention was to provide labelling reagents for the synthesis of labelled oligonucleotides in which the label is not subjected to a strong electron-acceptor effect and remains stable during the oligonucleotide synthesis.

An object of the present invention was also in particular to provide support materials for the synthesis of fluorescent-labelled oligonucleotides which on the one hand, ensure an adequately stable coupling of the fluorescent dye during the oligonucleotide synthesis and, on the other hand, do not influence the spectral properties of the fluorescent dye compared to derivatives coupled with a thiourea linker.

BRIEF DESCRIPTION OF THE INVENTION

Hence the present invention concerns a labelling reagent having the structure in which
  M is a detectable label
  L represents a linker of the structure —$(CH_2)p$- or the structure —$(CH_2)p$-CO—NH—
  Z is either CH or N,
  S is a cleavable protective group
  n, m and p are, independently of one another, natural numbers from 1–15,
  O-K is either a phosphoramidite,
  or K=-V-T, such that T is a solid phase support material and
  V is a linking group containing a cleavable bond.

Hence a subject matter of the present invention is also a labelled reactive support having the structure in which
  M is a detectable label
  L represents a linker of the structure —$(CH_2)p$- or the structure —$(CH_2)p$-CO—NH—

Z is either CH or N, n, m and p are, independently of one another, natural numbers from 1–15, S is a cleavable protective group and T is a solid phase support material.

The linker L preferably has the structure

—(CH$_2$)p-CO—NH— in which p is a natural number from 1–15.

Porous glass or polystyrene particles having a defined pore size are usually used as the solid phase support material. The cleavable protective group S is usually dimethoxytrityl (DMT), pixyl or a photochemically cleavable nitrobenzyl group such as NPEOC (Tetrahedron 53, p. 4247–4264 (1997)).

For numerous potential applications of the invention the reactive support is provided with a fluorescent dye such as fluorescein as a detectable label. If the fluorophore contains reactive groups such as hydroxy groups in the case of fluorescein, these hydroxy groups have to be protected in order to prevent an undesired reaction with the phosphoramidites during the oligosynthesis. Pivaloyl is for example a suitable protective group since it can be removed by cleavage under standard conditions after completion of the oligosynthesis.

A further subject matter of the invention is also the use of a molecule having the structure M-NH—CO—(CH$_2$)p-COOH in which p represents a natural number between 1 and 15 and M represents a detectable label, to prepare a reactive support according to the invention.

This synthesis is preferably carried out by a process comprising the following steps:

a) preparing a trifunctional spacer containing two reactive hydroxyl groups and one reactive amino group b) introducing a protective group such as DMT on a hydroxyl group c) converting the carboxylic acid group of the molecule described above into an activated ester preferably an N-hydroxysuccinimide ester d) coupling the activated ester to the reactive amino group of the trifunctional spacer e) coupling the hydroxyl group of the trifunctional spacer which is still free to the support material.

Alternatively the reactive support according to the invention can be prepared by using a trifunctional spacer having the structure HOOC—L—Z—(CH$_2$)n—OH
           |
          (CH$_2$)m
           |
          OH in which L represents a linker which has the structure —(CH$_2$)p- or the structure

—(CH$_2$)p-CO—NH— and p is a natural number between 1 and 15.

Such a process preferably comprises the following steps:

a) preparing the described trifunctional spacer b) introducing the protective group on a hydroxyl group c) activating the carboxylic acid group of the trifunctional spacer to form an activated ester d) reacting the active ester with the free amino group of the detectable molecule e) coupling the hydroxyl group that is still free to the support material.

A further subject matter of the invention is the use of the reactive support according to the invention to synthesize 3'-labelled nucleic acids such as (deoxy)-oligonucleotides and 3'-labelled nucleic acid molecules which have been synthesized with the aid of a support according to the invention and consequently have a new chemical structure at their 3'-end. This also especially concerns nucleic acid molecules which have a substituent at the 3'-position of the 3'-terminal ribose which has the substructure

—CH$_2$—CO—NH-M in which M is a detectable label such as a fluorescent dye.

The invention also concerns phosphoramidites having the structure

M—NH—CO—L—Z—(CH$_2$)n—O—S
              |
             (CH$_2$)m—O—K in which

M is a detectable label

L represents a linker of the structure —(CH$_2$)p- or the structure —(CH$_2$)p-CO—NH—

Z is either CH or N,

S is a cleavable protective group n, m and p are, independently of one another, natural numbers from 1–15, and O-K is a phosphoramidite.

In this connection the term "phosphoramidite" is understood to include all compounds known as phosphoramidites to a person skilled in the art (Beaucage, Methods in Molecular Biology, ed. S. Agrawal, Vol.20, p. 33–61, 1993).

The label is preferably a fluorescent dye such as fluorescein which is optionally provided with protective groups.

The present invention also concerns the use of the phosphoramidites according to the invention to synthesize labelled nucleic acids. Nucleic acids which have been labelled with the aid of these phosphoramidites are also a subject matter of the invention. Such molecules contain a substituent having the structural element —CH$_2$—CO—NH-M in which M denotes the detectable label such as the fluorescent dye. In a preferred embodiment the substituent is covalently bound to the 5'-position of the 5'-terminal ribose of the labelled nucleic acid.

DETAILED DESCRIPTION OF THE INVENTION

Within the scope of the present invention some of the terms used are defined as follows:

Reactive group denotes groups of a molecule which are able to react with another molecule under suitable conditions to form a covalent bond. Examples of reactive groups are hydroxyl groups, amino groups and carboxylic acid groups.

Protective group denotes molecules which react with one or several reactive groups of a molecule in such a manner that in a multistep synthesis reaction only one particular non-protected reactive group can react with the desired reaction partner. Examples of frequently used protective groups are dimethoxytrityl (DMT) which is preferably used to protect hydroxyl groups and Fmoc which is preferably used to protect amino groups.

Trifunctional spacers are molecules which have a central carbon or nitrogen atom and comprise three side chains that are essentially composed of carbon and each have a reactive group at the end.

Solid phase support material refers to polymeric substances that form a solid phase containing a reactive group on which other molecules can be immobilized. In the case of oligonucleotide synthesis this are usually porous glass beads having a defined pore size (CPG). Alternatively polystyrene resins and other organic U polymers and copolymers can also be used (J. Indian Chem. Soc. 1998, 75, 206–218). If the oligonucleotide should remain immobilized on the substrate after the synthesis, glass or semiconductor chips can also be used as a solid phase support material.

A labelled reactive support is understood as a solid phase support material on which another compound containing a detectable label and a still unprotected reactive group is immobilized. Carbon chains having a length of 1–15 C atoms are referred to as linkers. Such linker chains can additionally also have a single nitrogen atom or several nitrogen atoms. In addition the linkers can also contain a single ethylene glycol unit or several ethylene glycol units.

A detectable label is understood as substances that can be detected with the aid of analytical methods. These can for example be substances that can be detected with the aid of mass spectroscopy; immunological assays or with the aid of NMR. In particular detectable labels are also understood to include fluorescent dyes such as fluoresceins or rhodamines.

Phosphoramidites denotes molecules having a trivalent phosphorus atom which can be coupled to the 5'-terminal end of a nucleoside or nucleoside derivative. Thus phosphoramidites can be used to synthesize oligonucleotides. In addition to the (deoxy)-ribonucleotide phosphoramidites that are used for chain extension, there are also phosphoramidites derivatized with a label which can be used in analogous processes to label the oligonucleotide during or at the end of oligonucleotide synthesis (Beaucage, Methods in Molecular Biology, ed. S. Agrawal, vol. 20, p. 33–61 (1993)), (Synlett 10, 1667–1678 (1999)).

The term "oligonucleotide" encompasses in connection with the present invention not only (deoxy)-oligoribonucleotides but also all DNA and RNA derivatives such as methylphosphonates, phosphothioates or 2'-O-alkyl derivatives and DNA analogues such as LNA, HNA (18, p. 1365–1370 (1999)) and nucleic acids or analogues thereof which also contain modified bases such as 7-deazapurines as well as chimeras comprising different types of nucleic acids and analogues thereof.

A labelled reactive support having the structure has proven in the past to be particularly suitable for oligonucleotide syntheses. L in this connection denotes a linker. According to the prior art this linker contains an amide bond which directly links the carbon atom to the label.

T denotes a solid phase support material preferably CPG which is commercially available (e.g. Proligo, CPG Inc.). The surface of such commercial support materials is modified with amino groups.

The support T can be linked to the remainder of the molecule via a so-called linking group V containing a cleavable bond. Linking groups containing cleavable bonds are understood in the scope of the present invention as groups located between the trifunctional spacer and the solid phase support material that can be cleaved by a simple chemical reaction. These can be succinyl or oxalyl or other linking groups which contain a cleavable ester bond. Other linking groups are known to a person skilled in the art (J. Indian. Chem. Soc. 1998, 75, 206–218).

Such linking groups are essential for the application of the support material to synthesize oligonucleotides which are intended to be present in aqueous solution after completion of the synthesis. In contrast in the case that the oligonucleotide should remain on the surface of the support material after the synthesis when for example preparing nucleic acid arrays (U.S. Pat. No. 5,624,711, Nucl. Acids. Res. vol. 25, p. 1155–1161 (1997)), a cleavable linking group is unnecessary and rather a non-cleavable linking group is preferred.

The support material is linked via a carbon chain comprising 1–15 C atoms to a trifunctional central atom Z which is preferably also carbon or alternatively nitrogen. A further carbon chain containing 1–15 C atoms on the end of which a cleavable protective group S, preferably DMT is present, is located on this central C atom. This protective group can be cleaved by weak acid treatment before starting the oligonucleotide synthesis. Afterwards 3' phosphoramidite derivatives of (deoxy)-ribonucleosides can be coupled to the liberated reactive group.

The detectable label M is preferably a fluorescent dye. If such labels contain reactive groups that could interfere with the oligonucleotide synthesis, the fluorescent dye is provided with a protective group known to a person skilled in the art in order to prevent unspecific reactions during the course of an oligonucleotide synthesis. Fluorescent dyes such as fluorescein can be effectively protected by pivaloyl.

The detectable label is usually linked to the central atom via a special linker. This linker has the following characteristic structure according to the invention or in which p is a natural number between 1 and 15.

In other words this means that the orientation of the amide bond between the label M and linker L or central atom Z is inverted compared to the compounds known from the prior art.

Hence the partial structure is characteristic of the inventive structure of the linker.

This ensures that the electron-acceptor effect of the amide bond shown is substantially lower than that of the structure known from the prior art This has the advantage that for example in the case of a fluorescent dye label the spectral properties of the fluorescent dye conjugated according to the invention are almost identical to the spectral properties of a dye conjugated by the thiourea method due to the orientation of the amide bond. However, in comparison to thiourea coupling, the linker structure according to the invention leads to a much more stable compound which also remains stable during oligonucleotide synthesis.

The labelled reactive support according to the invention can be basically synthesized by two different methods. In a first embodiment a reactive trifunctional spacer containing two reactive hydroxyl groups and one reactive amino group is reacted with an NHS-activated carboxylic acid group of a detectable label. In an alternative method a trifunctional spacer containing a reactive carboxylic acid group is firstly converted into an activated ester and then reacted with a reactive amino group of a detectable molecule.

Both methods are part of the present invention and are thus further elucidated in the following. In general preparative methods in organic chemistry known to a person skilled in the art are used to carry out the individual steps of the synthesis. The stated methods only represent examples of alternatives and do not limit the scope of the present invention.

a) Preparation of a support according to the invention a starting with a trifunctional spacer containing a reactive amino group.

Serinol can for example be used as a commercially available spacer containing a central carbon atom and a free nitrogen atom. A trifunctional spacer containing a central nitrogen atom can be obtained from the commercially available compound 2-hydroxyethylhydrazine and oxirane.

In a first process step a protective group is introduced on one of the reactive hydroxyl groups of the trifunctional spacer such that this side chain cannot react with other reaction partners during the subsequent steps of the synthesis. Dimethoxytrityl (DMT) is usually introduced as the protective group by known methods (J. Am. Chem. Soc. 1963, 85, 3821). At the end of the reaction those molecules which only have one protective group are isolated by column chromatographic methods known to a person skilled in the art.

Detectable labelling substances M which have a free terminal amino group can be converted using organic methods of synthesis that are also known to a person skilled in the art by reaction with an appropriate activated dicarboxylic acid such as a dicarboxylic acid anhydride into a molecule having the structure while producing an amide bond, where the length p of the $CH_2$ chain is at least 1 and at most 15. Such compounds having a carboxylic acid residue can be converted under conditions known to a person skilled in the art into an N-hydroxysuccinimide ester by reaction with N-hydroxysuccinimide. In particular fluorescent dye molecules can be converted in this manner into a corresponding NHS-ester derivative. If the labelling group M contains free reactive groups such as hydroxy groups, these must, however, previously be provided with appropriate protective groups known to a person skilled in the art.

In a further reaction step the labelled NHS ester is coupled to the free amino group of the trifunctional spacer by standard methods. Subsequently the hydroxyl group of the trifunctional spacer that is still free is immobilized by conventional methods on the support material which is usually CPG. A derivatized support material which has a reactive group such as a hydroxyl, amino, thiol or carboxyl group is used for this purpose.

After the immobilization the reactive groups of the support material that are still free have to be deactivated by a so-called capping reaction known to a person skilled in the art (Pon R. T., in Methods in Molecular Biology, vol. 20. ed. S. Agrawal Humana Press Inc. New Jersey, chap. 19 p. 481–482 (1993)). Hence for example amino groups that are still free are deactivated by an acylation reaction.

Hence an immobilized compound having the structural element is generated by the method according to the invention and can be used in particular to synthesize 3'-terminally labelled nucleic acids as a result of the said advantageous properties.

b) Preparation of a support according to the invention starting with a trifunctional spacer containing a reactive carboxylic acid group.

Starting with a conventional trifunctional spacer containing two free hydroxyl groups and one free amino group a compound of the general structure is firstly prepared by reaction with a dicarboxylic acid using conventional methods while generating an amide bond, in which Z is either CH or N and

L represents a linker having the structure —$(CH_2)p$- or the structure —$(CH_2)p$-CO—NH— and at the same time m, n and p are each, independently of one another, a natural number between 1 and 15.

A compound of the following structure is preferred:

in which m, n and p are, independently of one another, a natural number between 1 and 15.

In a preferred manner one can also start with a spacer having a central nitrogen atom:

m, n and p are in this case also, independently of one another, natural numbers between 2 and 15. Molecules such as the commercially available bicine in which n and m=2 are particularly advantageous. The reason is that it is advantageous for the stability of such compounds when there are at least two C atoms between the central N atom and the two terminal hydroxyl groups.

Then a protective group such as DMT is introduced on one of the reactive hydroxyl groups such that this protective group cannot react with other reaction partners during the following steps of the synthesis. At the end of the reaction those molecules which only have one protective group are isolated by methods of preparative column chromatography known to a person skilled in the art.

Subsequently the carboxylic acid group that is still free is activated under conditions known to a person skilled in the art. In particular an activation using triphosgene and DMF has proven to be particularly suitable.

In a further step a detectable molecule containing a reactive amino group such as a fluorescent dye molecule can be coupled to the trifunctional spacer. A trifunctional spacer is formed in this manner in which, as described under a), a hydroxyl group is protected with dimethoxy-trityl, the central atom is linked to the labelling group via a linker and which contains a free hydroxy group.

Finally the hydroxyl group of the trifunctional spacer that is still free is immobilized on the support material which is usually CPG, by standard methods analogously to the process described under a). Again the reactive groups of the support material that are still free have to be deactivated after the immobilization by a so-called capping reaction known to a person skilled in the art.

In an alternative embodiment of the present invention the labelling reagent can be a non-nucleosidic phosphoramidite.

Similarly to the inventive process for the preparation of reactive supports, an intermediate product of the following general formula is firstly prepared in a first step:

in which M is a detectable label and Z is either CH or N. S denotes a cleavable protective group, L denotes a linker having the structure —(CH$_2$)p- or the structure —(CH$_2$)p-CO—NH— and n, m and p, independently of one another, denote natural numbers from 1–15.

In this embodiment the protective group S is preferably dimethoxytrityl. It is equally advantageous if reactive groups that may be present on the label are also provided with protective groups.

These precursors can then be converted in a second step by known methods into a phosphoramidite according to the invention by reaction of the hydroxyl group that is still free (e.g. B. Meyer R. B. in Methods in Mol. Biol. vol. 26 ed. S. Agrawal, Humana Press Inc. 1994, chapter 2 p. 80).

Such inventive phosphoramidites can be used to label nucleic acids and in particular to label oligonucleotides. The label can be introduced at the 5'-end, at the 3'-end or internally as a so-called "abasic site" in oligonucleotides.

In the case of a 5'-label at the 5'-position of the ribose of the 5'-terminal nucleotide the incorporation is carried out by conventional methods at the end of the oligonucleotide synthesis (Beaucage, Methods in Molecular Biology, ed. S. Agrawal, vol. 20, p. 33–61 (1993)). Subsequently the remaining protective group—usually DMT—is removed. Oligonucleotides are obtained in this manner which have a substituent containing the structural element —CH$_2$—CO—NH-M at the 5'-position of the 5'-terminal ribose.

After again removing the protective group introduced by the phosphoramidite, a chain extension in the 3'–5' direction can then be carried out on the free hydroxyl group as part of a classical oligonucleotide synthesis. An internally labelled nucleic acid molecule containing a so-called internal "abasic site" is formed in this manner.

Labelling at the 3'-end is carried out according to the following principle: Commercially available 3'-phosphate-CPG (e.g. Glenn Research) is used as the support. A phosphoramidite according to the invention is used in the first cycle of the synthesis. Since this contains an additional tritylated hydroxyl group, standard oligonucleotides synthesis can begin, after cleavage of the DMT protective group, at the hydroxyl group that is now free. After cleavage from the support, oligonucleotides are then obtained which have a substituent containing the structural element —CH$_2$—CO—NH-M at the 3'-position of the 3'-terminal ribose.

The invention is further characterized by the following examples:

EXAMPLE 1

Preparation of a dipivaloylfluorescein-NHS ester
A) Dipivaloylnitrofluorescein 8 ml (65 mmol) pivaloyl chloride (Merck 801276) was added dropwise to a suspension of 5 g (13 mmol) 4-nitrofluorescein (TCI 199) in a mixture of 100 ml dichloromethane, 8 ml pyridine and 6 ml dimethylformamide while cooling on ice. The resulting clear, yellow solution was subsequently stirred for 2.5 h at room temperature. In this process a white precipitate (pyridinium hydrochloride) forms which was removed by filtration. 20 ml dichloromethane and 50 ml water were added to the filtrate which was transferred to a separating funnel. The organic phase was separated and washed once with 50 ml water. The separated organic phase was dried over sodium sulfate and evaporated to dryness in a vacuum on a rotary evaporator. The residue obtained was recrystallized from 100 ml diisopropyl ether (yield: 6.5 g).

B) Dipivaloylaminofluorescein 6.5 g (11.9 mmol) dipivaloylnitrofluorescein was dissolved in 100 ml dioxane. Then 650 mg palladium/activated carbon (Merck 807104) dissolved in 20 ml ethanol was added and hydrogen was passed in for 2.5 h while shaking. Afterwards the mixture was filtered through a double filter (round filter+Seitz filter layers) and subsequently evaporated to dryness in a rotary evaporator under a vacuum. The residue obtained was separated over a silica gel 60 column (diameter=8.5 cm, height=30 cm). A mixture of ethyl acetate/hexane 2/1 (v/v) was used as the mobile solvent (yield: 3.0 g).

C) Dipivaloyl-4-aminoglutarylfluorescein

A mixture of 2.6 g (5 mmol) dipivaloylaminofluorescein, 2.3 g (20 mmol) glutaric anhydride, 123 mg (1 mmol) dimethylaminopyridine (Fluka 39405) and 1.4 ml (10 mmol) triethylamine in 75 ml chloroform were boiled for 4 hours under reflux. After cooling to room temperature 50 ml water was added and it was stirred for a further 15 min. The organic phase was separated in a separating funnel and washed twice with 50 ml water each time. After drying over sodium sulfate it was evaporated to dryness in a vacuum in a rotary evaporator.

The residue was separated over a silica gel 60 column (diameter=8.5 cm, height=30 cm). A mixture of toluene/ethyl acetate/methanol in a ratio of 4/1/2 (v/v/v) was used as the mobile solvent (yield: 3.0 g).

D) Dipivaloyl-4-aminoglutarylfluorescein NHS ester 1.4 g (12.2 mmol) N-hydroxysuccinimide was added under argon to a solution of 2.6 g (4.1 mmol) dipivaloyl-4-aminoglutarylfluorescein in 250 ml dry dichloromethane (4.1 mmol). Subsequently 1.93 ml (14.0 mmol) morpholinoethylisocyanide (14.0 mmol) was added and it was stirred for 18 h at room temperature. The solvent was removed by distillation in a rotary evaporator under a vacuum. A mixture of 600 ml ethyl acetate and 100 ml diethyl ether was added to the residue. The organic solution was washed in a separating funnel 3 times with 150 ml 0.2 N HCl each time and then once with 150 ml saturated sodium chloride solution. The separated organic phase was dried over sodium sulfate. After filtration the solvent was removed by distillation under a vacuum in a rotary evaporator. The residue was dried for 0.5 h in a high vacuum (yield: 2.7 g).

EXAMPLE 2

Preparation of a DMT-Fmoc Compound as a Trifunctional Spacer

A) N-Fmoc 1,3-dihydroxy-2-aminopropane 21.6 g Fmoc—NHS (Novabiochem. 01-63-001) (64 mmol) was dissolved in 300 ml dioxane and admixed successively with serinol (Aldrich 35,7898) (60 mmol), 200 ml water (VE) and 6.8 g sodium hydrogen carbonate (80 mmol). The mixture was then stirred overnight at room temperature. The resulting precipitate was removed by filtration on the following day.

1.2 l water and 50 ml saturated NaCl solution was added to the filtrate to precipitate the product. After the supernatant had been suction filtered over a glass frit, the product was dried overnight in a desiccator over calcium chloride. Subsequently it was separated over a silica gel 60 column (diameter=8.5 cm, height=30 cm). An ethyl acetate/methanol mixture in a volume ratio of 5/1 was used as the mobile solvent (yield: 12.35 g).

B) N-Fmoc 1-dimethoxytrityloxy 3-hydroxy-2-aminopropane

A solution of 13.85 g (41 mmol) dimethoxytrityl chloride in 55 ml dry pyridine was added to a solution of 12.19 g (38.9 mmol) N-Fmoc 1,3-dihydroxy-2-aminopropane in 60 ml dry pyridine under argon and stirred overnight at room temperature. Subsequently the solvent was removed under a vacuum in a rotary evaporator, the residue was dissolved in 500 ml ethyl acetate and extracted once with 250 ml water/250 ml saturated NaCl solution. The organic phase was separated and dried over sodium sulfate. After filtration the solvent was removed by distillation under a vacuum in a rotary evaporator.

Subsequently it was separated over silica gel. A mixture of toluene/ethyl acetate/methanol in a ratio of 4/1/0.5 (v/v/v) to which 0.1% (v) triethylamine had been added was used as the mobile solvent (yield: 15 g).

C) 1-dimethoxytrityloxy-3-hydroxy-2-aminopropane 14 g (22.7 mmol) N-Fmoc 1-dimethoxytrityloxy-3-hydroxy-2-aminopropane was dissolved in 200 ml ethyl acetate and subsequently 200 ml piperidine was added while stirring. After stirring overnight at room temperature it was evaporated to dryness in a vacuum on a rotary evaporator. The residue was separated on silica gel. Mobile solvent: toluene/ethyl acetate/methanol in a volume ratio of 4/1/0.5 to which 0.1% (v) triethylamine had been added (yield: 6.0 g).

EXAMPLE 3
Preparation of a fluorescein CPG according to the invention

A) Reaction of glutarylamino-bispivaloylfluorescein NHS ester containing 1-dimethoxytrityloxy-3-hydroxy-2-aminopropane (Preparation of an Inventive Trifunctional Spacer Substituted with Fluorescein and DMT).

2.7 g (3.7 mmol) glutarylamino-bispivaloylfluorescein NHS ester and 2.0 g (5.09 mmol) 1-dimethoxytrityloxy-3-hydroxy-2-aminopropane were stirred overnight in 2.5 ml pyridine while excluding moisture. Subsequently the solvent was removed by distillation under a vacuum on a rotary evaporator. The residue was separated on silica gel 60. A mixture of ethyl acetate/methanol in a ratio of 8/1 (v/v) to which 0.1% (v) triethylamine had been added served as the mobile solvent. Yield: 2.4 g (TLC: silica gel 60 Merck 105735 toluene/ethyl acetate/methanol, 4/1/1 Rf:0.45).

B) Succinylation (Preparation of a Trifunctional Spacer Substituted with Fluorescein, DMT and a Reactive Carboxyl Group).

A mixture of 2.33 g (2.3 mmol) product from A and 0.49 g (5 mmol) succinic anhydride and 61.5 mg (0.5 mmol) DMAP and 30.5 ml dry pyridine was stirred overnight under argon at room temperature. Subsequently the solvent was removed under a vacuum on a rotary evaporator. The residue was separated on silica gel 60. A mixture of toluene/ethyl acetate/methanol in a ratio of 4/1/1 (v/v/v) to which 0.1% (v) triethylamine had been added served as the mobile solvent (yield: 2.2 g). (TLC: silica gel 60 Merck 105735 toluene/ethyl acetate/methanol, 4/1/1 Rf=0.42).

C) Preparation of Fluorescein-CPG Having the Structure: (Preparation of a Fluorescein-CPG According to the Invention)

A suspension of 2.2 g (2.0 mmol) succinate from step B), 2.0 g (10.4 mmol) N-(3-dimethylaminopropyl)-N'-ethyl-carbodiimide hydrochloride (EDC) and 200 mg (1.64 mmol) DMAP was stirred under argon in a mixture of 80 ml dry DMF and 44 ml dry pyridine in a 500 ml round bottom flask until all of the EDC had dissolved. Then 28 g Icaa—CPG 500 A (CPG-Inc) was added. The suspension was subsequently gently shaken for 16 h at room temperature while excluding moisture.

Subsequently it was vacuum filtered over a D3 glass frit, the residue was successively washed with 220 ml DMF, 220 ml THF and 150 ml ether and subsequently sucked dry.

For the capping 80 ml pyridine and 22 ml acetanhydride were added to the CPG in a 500 ml flask and the mixture was gently shaken for 1 h at room temperature.

It was then vacuum filtered over a D3 glass frit and the residue was washed successively with 440 ml THF and 125 ml ether. The CPG material was subsequently dried for 4 h in a high vacuum (yield: 28.4 g).

D) Examination of the Loading by Means of Trityl Cleavage 4.37 mg of the CPG material was suspended in 25 ml DMT removal reagent (Roth 2257.2) and the absorbance A at 498 nm was measured (A=0.51).

$$\text{Epilson}_{498\ nm} DMT = 14300 (L*/mol*cm)$$

The calculation was as follows:

$$14.3(L*\text{mmol}^{-1}*\text{cm}^{-1})*25\ \text{ml}*A_{498\ nm}/\text{weight(mg)} = \mu\text{mol/g } CPG$$

$$14.3*25\ \text{ml}*0.514/4.37\ \text{mg} = 42.05\ \mu\text{mol/g } CPG$$

EXAMPLE 4

Preparation of a Fluorescein-CPG According to the Invention

A) Dimethoxytrityl-bicine

A solution of 3.38 g (10 mmol) dimethoxytrityl chloride dissolved in 50 ml pyridine was added while stirring vigorously to a mixture of 200 ml pyridine and 6.56 g (40 mmol) dry bicine. It was then stirred for 18 hours at room temperature and while excluding moisture. Subsequently the solvent was removed by distillation under a vacuum on a rotary evaporator. Afterwards 200 ml ethyl acetate was added and it was shaken for 10 min. The suspension was subsequently vacuum filtered. The residue was stirred for 10 min with 200 ml ethyl acetate and again vacuum filtered. The combined filtrates were concentrated to 30 ml under a vacuum on a rotary evaporator. 700 ml hexane was then added dropwise to the solution while stirring. This causes the product to flocculate. It was subsequently suction filtered, rewashed with 200 ml hexane and dried in a high vacuum (yield: 1.1 g).

B) N-(2-hydroxyethyl)-N (2-dimethoxytrityloxyethyl)-5-(2-amino-ethylcarboxamido)-bispivaloylfluorescein 0.52 g (1.75 mmol) bistrichloromethyl carbonate (triphosgene) was dissolved in 30 ml dry THF under argon while stirring. Subsequently 0.370 ml DMF was added while cooling on ice and stirred for one hour at 0° C. After heating to room temperature, 2.20 ml triethylamine and then a mixture of 2.33 g (5 mmol) dimethoxytritylbicine and 2.60 g (5 mmol) dipivaloyl-(4'-amino)fluorescein dissolved in 20 ml THF were added and it was then stirred for 16 hours at room temperature.

Subsequently the solvent was removed by distillation under a vacuum on a rotary evaporator. The residue was separated on silica gel 60. A mixture of toluene/ethyl acetate/methanol in a ratio of 4/1/1 (v/v/v) to which 0.1% triethylamine had been added served as the mobile solvent (yield: 0.6 g).

Succinylation and coupling to the CPG support were carried out as described in example 3.

EXAMPLE 5

Synthesis and Purification of a 3'-labelled Fluorescein 27 mer Oligonucleotide

The synthesis was carried out with the aid of an automated DNA synthesizer (Applied Biosystems, model ABI 392-08). The synthesis scale was 1 μmol: For this 24 mg of the fluorescein-CPG material from example 3 was filled into an empty synthesis column (Glenn Research) and the column was mounted in the appropriate position on the synthesizer. Standard 3'-phosphoramidites ([(MeO)$_2$Tr]ib$^2$G$_d$, [(MeO)$_2$Tr]bz$^6$A$_d$, [(MeO)$_2$Tr]bz$^4$C$_d$, [(MeO$_2$Tr]T$_d$) were used for the synthesis.

The oligomer synthesis followed the regular phosphoramidite protocol for the DNA synthesizer in the trityl off mode. The oligonucleotide was cleaved or deprotected with 25% NH3/H2O (8 h at 55° C.). An ion exchange chromatography on MonoQ (5.0×50 mm column from Amersham Pharmacia Biotech) was used for the purification (A: 10 mM sodium hydroxide/water B: 1 M sodium chloride in 10 mM sodium hydroxide/water, flow rate: 1 ml/min from 0% B to 100% B within 30 min). The labelled oligomer is desalted by dialysis or gel filtration and lyophilized.

Figure 1:
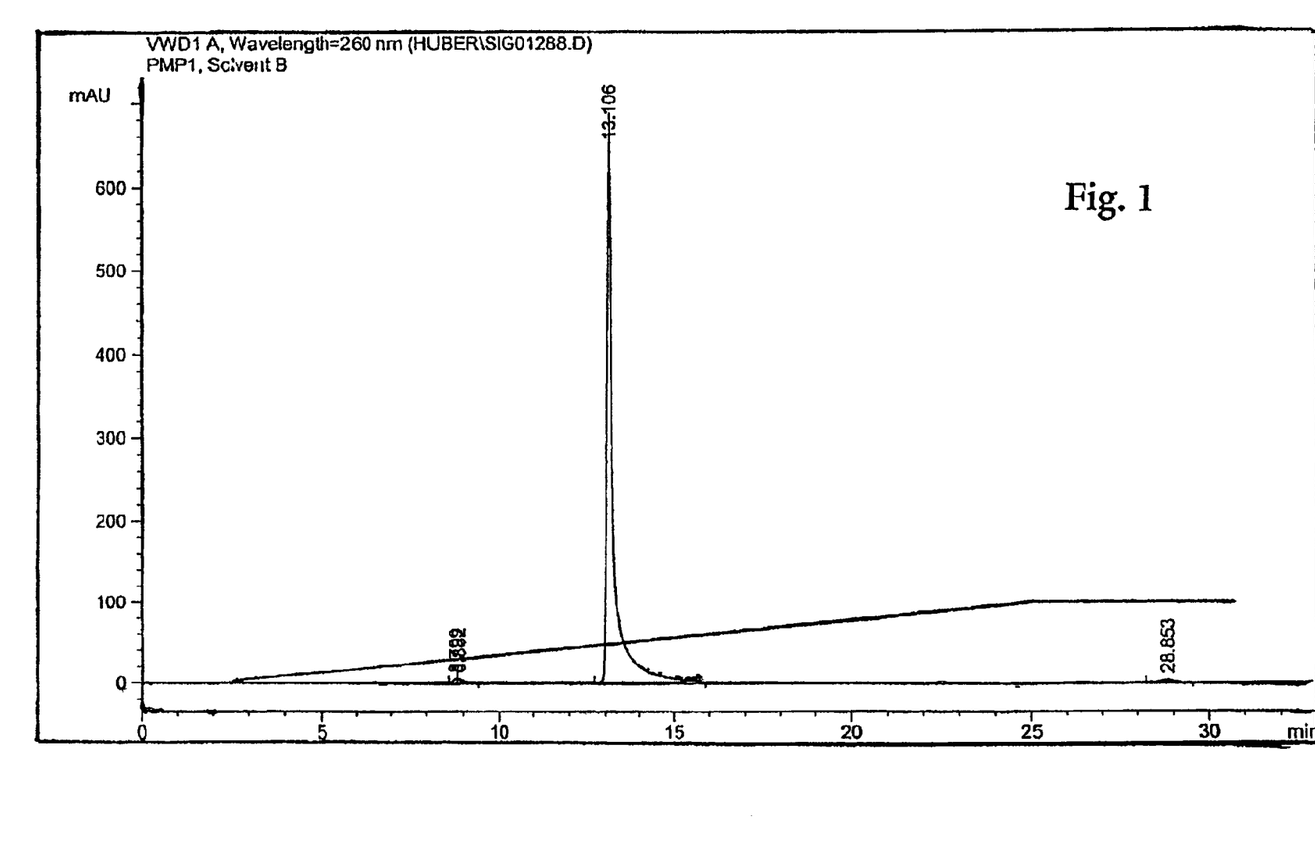

FIG. 1 shows a HPLC chromatogram. The HPLC conditions were as follows: column: RP18 Bischoff Hypersil ODS 5 μNC (250×4.6 mm) part 25461805, buffer A: 0.1 M triethylammonium acetate pH 6.8, buffer B: 1 1 A+1 1 acetonitrile, gradient: 2 min from 0% B to 100% B in 23 min, 100% B for 8 min, flow rate: 1 ml/min. Detection at 260 nm.

Figure 2:
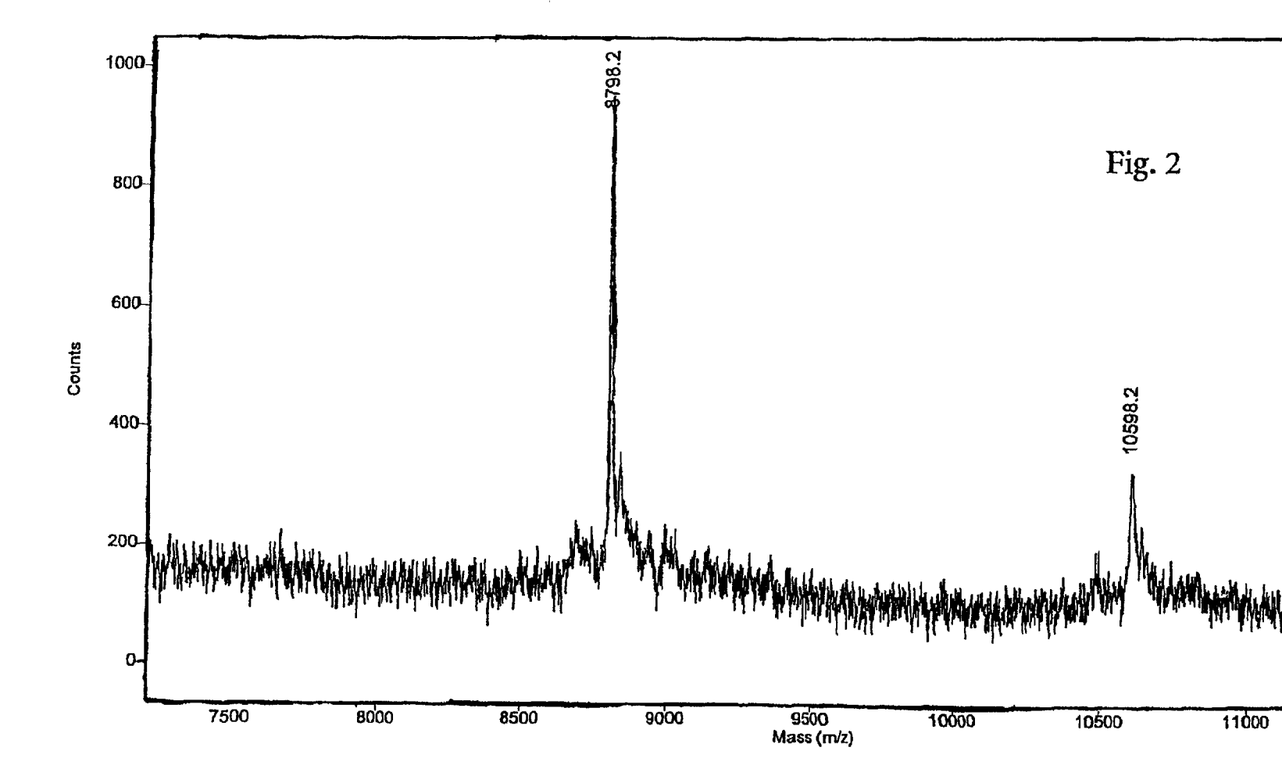

FIG. 2 shows a MALDI MS spectrum (Voyager DE, PerSeptive Biosystems, matrix: 3 hydroxypicolinic acid). The peak at m/z=8798.2 corresponds to the mass of the oligonucleotide, the peak at m/z=10598.2 is an internal standard.

Both figures show that a 3'-labelled oligonucleotide according to the invention can be synthesized with high purity.

BRIEF DESCRIPTION OF THE FIGURES

FIG. 1:

HPLC chromatogram of an oligonucleotide synthesized according to the invention with a fluorescein label at the 3'-end.

FIG. 2:

Mass spectrogram of the same oligonucleotide synthesized according to the invention.

What is claimed is:

1. A labelling reagent having the structure in which

M is a detectable label,

L represents a linker having the structure —(CH$_2$)p- or the structure —(CH$_2$)p-CO—NH—, Z is CH or N,

X is a cleavable protective group, n, m and p are, independently of one another, natural numbers from 1–15, and O-K is a phosphoramidite.

2. The labelling reagent as claimed in claim 1, wherein the detectable label M is a fluorescent dye.

3. A labelled reactive support having the structure in which

M is a detectable label,

L represents a linker having the structure —(CH$_2$)p- or the structure —(CH$_2$)p-CO—NH—, Z is CH or N, X is a cleavable protective group, n, m and p are, independently of one another, natural numbers from 1–15, T is a solid phase support material, and V is a linking group which contains a cleavable bond.

4. A support as claimed in claim 3, wherein the support material consists of glass particles having a defined pore size.

5. A support as claimed in claim 3, wherein the detectable label M is a fluorescent dye.

6. A process for the production of a labelled reactive support comprising:

a) providing a trifunctional spacer containing two reactive hydroxyl groups and one reactive amino group, b) introducing a protective group on one of the hydroxyl groups, c) providing a molecule having the structure M-NH—CO—(CH$_2$)p-COOH in which p represents a natural number between 1 and 15 and M is a detectable label and converting the carboxylic acid group of the molecule into an activated ester, d) coupling the activated ester to the reactive amino group of the trifunctional spacer, and e) coupling the hydroxyl group of the trifunctional spacer which is still free to the support material, thereby forming the labelled reactive support.

7. A process for the production of a labelled reactive support comprising:

f) providing a trifunctional spacer having the structure in which
Z is either CH or N, L is a linker having the structure —$(CH_2)_p$- or the structure —$(CH_2)_p$-CO—NH—, and m, n and p are, independently of one another, a natural number between 1 and 15, g) introducing a protective group on one of the hydroxyl groups, h) converting the carboxylic acid group of the trifunctional spacer into an activated ester, i) coupling a detectable molecule containing a free amino group by reacting the active ester with the amino group, and j) coupling the second of the hydroxyl groups to the support material, thereby forming the labelled reactive support.

* * * * *